(12) United States Patent
Fritz et al.

(10) Patent No.: US 8,809,613 B2
(45) Date of Patent: Aug. 19, 2014

(54) METHOD FOR PREPARING LINEAR ALPHA-OLEFINS

(75) Inventors: Peter M. Fritz, Unterhaching (DE); Heinz Bölt, Wolfratshausen (DE); Andreas Meiswinkel, Munich (DE); Carsten Taube, Ebersberg (DE); Florian Winkler, Munich (DE); Volker Göke, Wolfratshausen (DE); Wolfgang Müller, Munich (DE); Anina Wöhl, Pullach (DE); Richard Schneider, Uffing (DE); Uwe Rosenthal, Lambrechtshagen (DE); Helmut Fritz, Munich (DE); Bernd H. Müller, Rostock (DE); Normen Peulecke, Rostock (DE); Stephan Peitz, Rostock (DE); Bhaskar Reddy Aluri, Bangalore (IN); Mohammed Al-Hazmi, Riyadh (SA); Shahid Majeed Azam, Riyadh (SA); Fuad Mosa, Riyadh (SA); Abdullah Al-Dugathier, Riyadh (SA)

(73) Assignees: Saudi Basic Industries Corporation (SA); Linde AG (DE)

( * ) Notice: Subject to any disclaimer, the term of this patent is extended or adjusted under 35 U.S.C. 154(b) by 0 days.

(21) Appl. No.: 13/386,618

(22) PCT Filed: May 28, 2010

(86) PCT No.: PCT/EP2010/003285
§ 371 (c)(1),
(2), (4) Date: Mar. 29, 2012

(87) PCT Pub. No.: WO2011/009509
PCT Pub. Date: Jan. 27, 2011

(65) Prior Publication Data
US 2012/0184692 A1    Jul. 19, 2012

(30) Foreign Application Priority Data
Jul. 24, 2009 (EP) .................................... 09009599

(51) Int. Cl.
*C07C 2/08* (2006.01)
(52) U.S. Cl.
USPC ............ 585/832; 585/520; 585/522; 585/523
(58) Field of Classification Search
CPC ................ C07C 2/06; C07C 2/04; C07C 2/24
See application file for complete search history.

(56) References Cited

U.S. PATENT DOCUMENTS

| 3,862,257 | A | 1/1975 | Buben et al. |
| 4,486,615 | A | 12/1984 | Langer, Jr. |
| 4,783,573 | A | 11/1988 | Shiraki et al. |
| 5,811,619 | A | 9/1998 | Commereuc |
| 6,576,721 | B2 | 6/2003 | Kobayashi et al. |
| 2010/0217058 | A1 | 8/2010 | Fritz et al. |
| 2011/0046429 | A1* | 2/2011 | Aliyev et al. ................. 585/527 |

FOREIGN PATENT DOCUMENTS

| CA | 2036473 | | 2/1991 |
| CN | 1107828 | A | 9/1995 |
| EP | 0241596 | A1 | 10/1987 |
| EP | 0295690 | A2 | 12/1988 |
| FR | 2857964 | A1 | 1/2005 |
| JP | 6341430 | A | 2/1988 |
| JP | 3220135 | A | 9/1991 |
| JP | H0853374 | | 2/1996 |
| JP | 10218800 | A | 8/1998 |
| WO | 0147839 | A1 | 7/2001 |
| WO | 2007016994 | | 2/2007 |

OTHER PUBLICATIONS

DE19807226A1; Oct. 15, 1998; Abstract Only; 2 pages.
DE433814C12; Mar. 16, 1995; Abstract Only; 1 page.
Eller, et al., "Amines, Aliphatic" in Ullmann's Encyclopedia of Industrial Chemistry, Wiley-VCH, 2002, 647-698.
Fabri, et al., "Xylenes" in Ullmann's Encyclopedia of Industrial Chemistry, Wiley-VCH, 2002, pp. 643-663.
JP03-103406; Apr. 30, 1991; Abstract Only; 1 page.
International Search Report; International Application No. PCT/EP2009/000030; International Filing Date; Jan. 7, 1991; 3 pages.
Written Opinion; International Application No. PCT/EP2009/000030; International Filing Date; Jan. 7, 2009; 8 pages.

(Continued)

*Primary Examiner* — Tam M Nguyen
(74) *Attorney, Agent, or Firm* — Cantor Colburn LLP

(57) ABSTRACT

The present invention relates to a method for preparing linear alpha-olefins (LAO) by oligomerization of ethylene in the presence of a solvent and homogeneous catalyst, comprising the steps of:

(i) feeding ethylene, solvent and catalyst into an oligomerization reactor,
(ii) oligomerizing the ethylene in the reactor,
(iii) removing a reactor outlet stream comprising solvent, linear alpha-olefins, optionally unreacted ethylene and catalyst from the reactor via a reactor outlet piping system,
(iv) dosing at least one additive selected from the group consisting of alcohols, poly-ethylene glycols, polyethylene glycol monoethers, polyethylene glycol diethers, polyamines, amines, amino alcohols and surfactants,
(v) transferring the reactor outlet stream containing the additive to a catalyst deactivation and removal section, and
(vi) deactivating the catalyst with caustic and removing the deactivated catalyst from the reactor outlet stream,
wherein the residence time of the additive in the reactor outlet stream prior to mixing with caustic is at least 1 second preferably at least 5 seconds, more preferably at least 10 seconds.

20 Claims, No Drawings

(56) References Cited

OTHER PUBLICATIONS

International Search Report; International Application No. PCT/EP2010/003285; International Filing Date May 28, 2010; 3 pages.
Written Opinion; International Application No. PCT/EP2010/003285; International Filing Date May 28, 2010; 8 pages.
English Abstract of Japanese Patent No. 03220135A; Date of Publication Sep. 27, 1991; 2 pages.
English Abstract of Japanese Patent No. 10218800A; Date of Publication Aug. 18, 1998; 2 pages.
English Abstract of Chinese Patent No. 1107828A; Date of Publication Sep. 6, 1995; 1 page.
English Abstract of Japanese Patent No. 6341430A; Date of Publication Feb. 22, 1988; 2 pages.
European Search Report for Application No. 09009599.3-2103 ; Date of mailing Dec. 10, 2009. 4 pages.

* cited by examiner

METHOD FOR PREPARING LINEAR ALPHA-OLEFINS

The present invention relates to a method for preparing linear alpha-olefins (LAO).

Processes for the oligomerization of ethylene utilizing homogeneous catalysts are widely known. For example, DE 43 38 414 C1 discloses a process for the oligomerization of ethylene to obtain linear alpha-olefins, where ethylene is catalytically converted in an empty tubular reactor utilizing a catalyst comprising a zirconium component and an aluminum component. The process is advantageously carried out in a continuous mode wherein gaseous and liquid outlet streams are obtained. The liquid outlet stream usually contains solvent, catalyst, dissolved ethylene and linear alpha-olefins. The catalyst may be preferably deactivated by caustic. Preferably, the deactivated catalyst is also extracted from the phase containing solvent, ethylene and alpha-olefins.

DE 198 07 226 A1 discloses the deactivation of the oligomerization catalyst with an aqueous solution of sodium hydroxide (caustic), wherein the deactivated catalyst is transferred from the organic phase into the aqueous phase.

From operational experience it was learned that the deactivation step has to be performed fast and effectively. Otherwise, there is a chance of product degradation by unwanted side reactions having influence on the product purity. Catalyst removal efficiency can be enhanced by static or active mixing devices. However, these systems turned out to be not optimal for the application due to high installations costs, respective intensive maintenance requirements.

As further disadvantage of the known processes was found that both formation of organic chlorides as well as of alkylated toluenes by Friedel-Crafts-alkylation occurs.

It is therefore an object of the present invention to provide a method for preparing linear alpha-olefins which overcomes the drawbacks of the prior art, especially to provide a method including deactivation and removal of the catalyst resulting in an improved product purity, suppression of unwanted side reactions, less energy requirements for mixing, no requirement for sophisticated mixing devices and allowing Online Cleaning of piping and equipment. Also, the formation of organic chlorides and of alkylated toluenes by Friedel-Crafts-alkylation shall be prevented.

This object is achieved by a method for preparing linear alpha-olefins (LAO) by oligomerization of ethylene in the presence of a solvent and homogeneous catalyst, comprising the steps of:
(i) feeding ethylene, solvent and catalyst into an oligomerization reactor,
(ii) oligomerizing the ethylene in the reactor,
(iii) removing a reactor outlet stream comprising solvent, linear alpha-olefins, optionally unreacted ethylene and catalyst from the reactor via a reactor outlet piping system,
(iv) dosing at least one additive selected from the group consisting of alcohols, poly-ethylene glycols, polyethylene glycol monoethers, polyethylene glycol diethers, polyamines, amines, amino alcohols and surfactants,
(v) transferring the reactor outlet stream containing the additive to a catalyst deactivation and removal section, and
(vi) deactivating the catalyst with caustic and removing the deactivated catalyst from the reactor outlet stream,
wherein the residence time of the additive in the reactor outlet stream prior to mixing with caustic is at least 1 second, preferably at least 5 seconds, more preferably at least 10 seconds.

It is preferred that the additive is selected from MOR, HO—$(CH_2\text{-}CH_2)_n$—OH, HO—$(CH_2\text{-}CH_2)_n$—OR, RO—$(CH_2\text{-}CH_2)_n$—OR, $R'_2N$—$[(CH_2)_n]$—$NR'_2$, $R'_3N$, $R'_2N$—$[(CH_2)_n]$—OR' with M alkali metal, R=alkyl or aryl, R'=H, alkyl or aryl and n=3-300.

Preferably, the amine is an organic amine, preferably a primary, secondary, tertiary or cyclic amine, more preferably selected from t-butyl amine, triethyl amine, cyclopentyl amine, t-octyl amine, n-heptyl amine, 2-heptyl amine, hexyl amine, 2-ethylhexyl amine, dihexyl amine, 1,6-diamino hexane, tributyl amine, 1,8-diamino octane, n-dodecyl amine, 3-ethylheptyl amine and tris-2-ethyl hexyl amine.

More preferred the additive is added continously into the actor outlet stream.

In one embodiment, the additive is added in an amount of 500 to 5000 wt ppm referred to the flow rate of the reactor outlet stream.

The amount of dosing is determined by the following two issues
  The amount required in a certain stochiometric ratio to the catalyst and cocatalyst rates as introduced into the LAO reactor
  The amount obtained from practical operational experience in order to realize the described online cleaning effects for the reactor outlet piping.

Even preferred, the additive is soluble in an organic phase containing linear alpha-olefins.

In a further preferred embodiment the additive is substantially insoluble or has a low solubility water or a mixture of water and caustic.

The additive may be preferably removed from the reactor outlet stream or a product fraction by distillation, extraction, adsorption or ion exchange.

More preferably, the removed additive is recycled into the reactor outlet stream when removed from the reactor.

In one preferred embodiment the additive is mixed with the reactor outlet stream by means of a mixing device, preferably a static mixer, a dynamic mixer, an ultrasonic mixer or a Venturi mixing nozzle.

It is preferred that the catalyst comprises a zirconium salt of organic acid and at least one organoaluminum compound.

Even preferred, the zirconium salt has the formula $ZrCl_{4-m}X_m$, wherein X=OCOR or $OSO_3R'$ with R and R' being independently alkyl, alkene or aryl, preferably phenyl, and wherein $0 \leq m \leq 4$.

It is further preferable that the at least one aluminum compound has the general formula $R^1_n Al_3 \cdot n$ or $Al_2 Y_3 R^1_3$, wherein $R^1$ represents an alkyl group having from 1 to 20 carbon atoms, Y represents Cl, Br or I, n is any number within the range $1 \leq n \leq 2$.

Surprisingly, it was found that dosing an additive selected from the group as disclosed above into the reactor outlet stream prior to the mixing of the reactor outlet stream with aqueous caustic only under certain, very specific conditions Significantly improves the efficiency of the catalyst removal section without obtaining any unwanted side reactions. Thus, the product purity can be improved. It was surprisingly found that there is a minimum residence time required for the additive until its impact on the system is evoluted. This minimum residence time is at least 1 second.

It was also found that a simple combination of amine dosing and a caustic deactivation will not at all be sufficient for the envisaged purpose. It is a main feature of the invention that surprisingly a certain minimum residence time between the dosing of the additive and the caustic is required.

All the additives disclosed are found to be responsible to prevent Friedel-Crafts-alkylations of the solvent utilized, as well as the formation of organic chlorides, especially by preventing the formation of HCl which forms with LAOs the organic chlorides, or with the formed organic chlorides and the solvent, preferably toluene, alkylated solvents.

Further, it is important to note that the location of addition of the additive is essential. For example, additive dosing into the caustic stream will not work, as well as simultaneous mixing of all streams, i.e. additive stream, reactor outlet stream and caustic stream, will not resolve all these issues. Rather, it is absolutely necessary that the additive is introduced into the reactor outlet stream close to the LAO reactor outlet, with a sufficient residence time prior to the mixing point with the caustic stream.

Without wishing to be bound to any theory, it is believed that the additive utilized in the inventive method may reduce the interfacial tension between the hydrocarbon LAO phase and the aqueous caustic phase, leading to the formation of smaller droplet sizes, and finally enhancing the solubility of the catalyst deactivation products in the aqueous caustic phase.

Only in case that the additive is dosed into actor outlet stream as illustrated, the following benefits can be achieved:
  effective mixing of LAO/caustic turned out to be much easier,
  product purities were improved due to suppression of unwanted side reactions,
  inhomogenity and hot spots in the LAO/caustic mixing step were not observed anymore, and
  maintenance requirements for a mixer are reduced.
  fouling/plugging of LAO reactor outlet piping is avoided due to the online-cleaning effect (i.e. removal of rust particles and materials from equipment surfaces, and pipe walls, by utilization of tenside effects).

Additional features and advantages of the present invention will now become apparent from the detailed description of a preferred embodiment thereof.

Ethylene is oligomerized in a suitable reactor, for example an empty tubular reactor as disclosed in DE 43 38 414 C1, utilizing a catalyst comprising a zirconium compound and an aluminum component. A suitable zirconium component is zirconium tetraisobutyrate, and a suitable aluminum component is ethyl aluminum sesquichloride.

The oligomerization is carried out under conditions (temperature, pressure, etc.) known in the art. Ethylene, solvent and catalyst are introduced and oligomerization is initiated, From the reactor, a liquid organic outlet stream is discharged into a reactor outlet piping system containing solvent, for example toluene, catalyst, ethylene dissolved in the solvent, and linear alpha-olefins. To this liquid organic outlet stream is dosed an additive selected from the group of non-ionic surfactants and amines, for example n-dodecyl amine. Mixing of the reactor outlet stream and the additive is for at least 1 second, prior to the addition of caustic thereto in a catalyst deactivation and removal section. However, the residence time shall not exceed a period of 100 seconds, since otherwise the additive is already deactivated by undergoing of different unwanted reaction steps and has lost its activity for the envisaged positive effects. The catalyst is then deactivated by caustic and removed from the outlet stream, The caustic phase may contain alkali metal hydroxide, preferably NaOH and/or KOH. After deactivation the deactivated catalyst will be present in the aqueous phase and can be removed as known the art.

After the catalyst deactivation and removal section, the amine can be removed from the LAO products (the remaining reactor outlet stream) by conventional distillation, extraction, ion exchange or adsorption, Remaining traces of the amine in the products can be additionally removed by adequate guard adsorbers, depending on the required product specification.

The prevention of Friedel-Crafts-alkylation was demonstrated by the following experiments:

LABORATORY EXPERIMENT NO. 1

Basic Experiment without Additive

In the laboratory 20 ml toluene, 10 ml 1-hexene, 5 ml EASC solution and 20 ml ZrCl4 solution were mixed in a flask at ambient temperature and under inert nitrogen atmosphere.

Under intensive stirring the mixture was quenched with 50 ml sodium hydroxide solution of 20 wt %.

Then the stirring has been switched off. After the phase separation of the hydrocarbon phase and the aqueous phase by gravity the hydrocarbon phase has been analyzed and shows high quantities of alkylated toluene.

LABORATORY EXPERIMENT NO. 2

Experiment with an Amine as an Additive (30 Seconds Residence Time)

In the laboratory 20 ml toluene, 10 ml 1-hexene, 5 ml EASC solution and 20 ml ZrCl4 solution and 1 ml of ethyl-hexyl-amine were mixed in a flask at ambient temperature and under inert nitrogen atmosphere for 30 seconds.

Under intensive stirring the mixture was quenched with 50 ml sodium hydroxide solution of 20 wt %.

Then the stirring has been switched off. After the phase separation of the hydrocarbon phase and the aqueous phase by gravity the hydrocarbon phase has been analyzed and shows no alkylated toluene.

LABORATORY EXPERIMENT NO. 3

Experiment with Amine as an Additive (Simultaneous Addition)

In the laboratory 10 ml toluene, 10 ml 1-hexene, 5 ml EASC solution and 20 ml ZrCl4 solution were mixed in a flask at ambient temperature and under inert nitrogen atmosphere. In a second flask 10 ml toluene and 1 of ethyl-hexyl-amine were Mixed.

Under intensive stirring both mixtures were poured in a 50 ml sodium hydroxide solution of 20 wt % simultaneously.

Then the stirring has been switched off. After the phase separation of the hydrocarbon phase and the aqueous phase by gravity the hydrocarbon phase has been analyzed and shows some alkylated toluene but less than in Experiment No 1.

LABORATORY EXPERIMENT NO. 4

Experiment with Amine as an Additive in the Sodium Hydroxide Solution

In the laboratory 20 ml toluene, 10 ml 1-hexene, 5 ml EASC solution and 20 ml ZrCl4 solution were mixed in a flask at ambient temperature and under inert nitrogen atmosphere.

Under intensive stirring this mixture was quenched with a mixture of 50 ml sodium hydroxide solution of 20 wt % and 1 ml of ethyl-hexyl-amine.

Then the stirring has been switched off After the phase separation of the hydrocarbon phase and the aqueous phase by gravity the hydrocarbon phase has been analyzed and shows almost the same amount of alkylated toluene as in Experiment No 1.

These simple experiments clearly confirm the importance and positive effect of the combination of an additive and the caustic for the prevention of undesired side reactions in catalyst deactivation and removal section of the LAO process. It becomes clear that the positive effect of the additive is also a function of the residence time of the additive in the reactor outlet stream prior to mixing with caustic.

The features disclosed in the following description and in the claims may, both separately and in any combination thereof, be material for realizing the invention in diverse forms thereof.

The invention claimed is:

1. A method for producing linear alpha-olefins (LAO) by oligomerization of ethylene in the presence of a reaction feed comprising a solvent and a homogeneous catalyst, comprising the steps of:
   (i) contacting ethylene with the reaction feed under oligomerization conditions and producing a reaction product comprising linear alpha-olefins the solvent and the catalyst,
   (ii) dosing said reaction product with at least one additive selected from the group consisting of alcohols, polyethylene glycols, polyethylene glycol monoethers, polyethylene glycol diethers, polyamines, amines, amino alcohols and surfactants,
   (iii) then treating the dosed reaction product with caustic to deactivate the catalyst in the reaction product, wherein the residence time of the additive in the dosed reaction product prior to treating the dosed reaction product with caustic is at least 10 seconds and does not exceed 100 seconds.

2. The method according to claim 1, wherein the additive is selected from MOR, HO—$(CH_2$—$CH_2)_n$—OH, HO—$(CH_2$—$CH_2)_n$—OR, RO—$(CH_2$—$CH_2)_n$—OR, R'$_2$N—$[(CH_2)_n]$—NR'$_2$, R'$_3$N, R'$_2$N—$[(CH_2)_n]$—OR' with M=alkali metal, R=alkyl or aryl, R'=H, alkyl or aryl and n=3-300.

3. The method according to claim 1, wherein the additive is a primary, secondary, tertiary or cyclic organic amine.

4. The method according to claim 3, wherein the additive is selected from t-butyl amine, triethyl amine, cyclopentyl amine, t-octyl amine, n-heptyl amine, 2-heptyl amine, hexyl amine, 2-ethylhexyl amine, dihexyl amine, 1,6-diamino hexane, tributyl amine, 1,8-diamino octane, n-dodecyl amine, 3-ethylheptyl amine and tris-2-ethyl hexyl amine.

5. The method according to claim 4, wherein the concentration of the additive in the reaction product is between 500 to 5000 wt ppm.

6. The method according to claim 3, wherein the additive is soluble in an organic phase containing linear alpha-olefins and has a solubility in water of less than 5 mol %, and the concentration of the additive in the reaction product is between 500 to 5000 wt ppm.

7. The method according to claim 5, wherein the additive is soluble in an organic phase containing linear alpha-olefins and has a solubility in water of less than 5 mol %.

8. The method according to claim 6, wherein the additive is recovered from the caustic treated reaction product and is used in the dosing of the reaction product in step (ii).

9. The method according to claim 7, wherein the additive is recovered from the caustic treated reaction product and is used in the dosing reaction product in step (ii).

10. The method according to claim 1, wherein said dosing comprises mixing said additive into said reaction product using static mixer, a dynamic mixer, an ultrasonic mixer or a Venturi mixing nozzle.

11. The method according to claim 10, wherein the catalyst comprises a zirconium salt of an organic acid and at least one organoaluminum compound, said zirconium salt has the formula $ZrCl_{4-m}X_m$, wherein X=$OCOR$ or $OSO_3R'$ with R and R' being independently alkyl, alkene or aryl and $0 \leq m \leq 4$, wherein said at least one organoaluminum compound has the general formula $R^1{}_n Al_{3-n}$, or $Al_2Y_3R^1{}_3$, wherein $R^1$ represents an alkyl group having from 1 to 20 carbon atoms, Y represents Cl, Br or I, and n is 1 or 2.

12. The method according to claim 2, wherein said dosing comprises mixing said additive into said reaction product using a static mixer, a dynamic mixer, an ultrasonic mixer or a venture mixing nozzle.

13. The method according to claim 12, wherein the catalyst comprises a zirconium salt of an organic acid and at least one organoaluminum compound, said zirconium salt has the formula $ZrCl_{4-m}X_m$, wherein X=$OCOR$ or $OSO_3R'$ with R and R' being independently alkyl, alkene or aryl and $0 \leq m \leq 4$, and wherein said at least one organoaluminum compound has the general formula $R^1{}_n Al_{3-n}$, or $Al_2Y_3R^1{}_3$, wherein $R^1$ represents an alkyl group having from 1 to 20 carbon atoms, Y represents Cl, Br or I, and n is 1 or 2.

14. The method according to claim 4, wherein said dosing comprises mixing said additive into said reaction product using a static mixer, a dynamic mixer, an ultrasonic mixer or a venture mixing nozzle.

15. The method according to claim 14, wherein the catalyst comprises a zirconium salt of an organic acid and at least one organoaluminum compound, said zirconium salt has the formula $ZrCl_{4-m}X_m$, wherein X=$OCOR$ or $OSO_3R'$ with R and R' being independently alkyl, alkene or aryl and $0 \leq m \leq 4$, and wherein said at least one organoaluminum compound has the general formula $R^1{}_n Al_{3-n}$, or $Al_2Y_3R^1{}_3$, wherein $R^1$ represents an alkyl group having from 1 to 20 carbon atoms, Y represents Cl, Br or I, and n is 1 or 2.

16. The method according to claim 6, wherein said dosing comprises mixing said additive into said reaction product using a static mixer, a dynamic mixer, an ultrasonic mixer or a venture mixing nozzle.

17. The method according to claim 16, wherein the catalyst comprises a zirconium salt of an organic acid and at least one organoaluminum compound, said zirconium salt has the formula $ZrCl_{4-m}X_m$, wherein X=$OCOR$ or $OSO_3R'$ with R and R' being independently alkyl, alkene or aryl and $0 \leq m \leq 4$, and wherein said at least one organoaluminum compound has the general formula $R^1{}_n Al_{3-n}$, or $Al_2Y_3R^1{}_3$, wherein $R^1$ represents an alkyl group having from 1 to 20 carbon atoms, Y represents Cl, Br or I, and n is 1 or 2.

18. The method according to claim 7, wherein said dosing comprises mixing said additive into said reaction product using a static mixer, a dynamic mixer, an ultrasonic mixer or a venture mixing nozzle.

19. The method according to claim 18, wherein the catalyst comprises a zirconium salt of an organic acid and at least one organoaluminum compound, said zirconium salt has the formula $ZrCl_{4-m}X_m$, wherein X=$OCOR$ or $OSO_3R'$ with R and R' being independently alkyl, alkene or aryl and $0 \leq m \leq 4$, and wherein said at least one organoaluminum compound has the general formula $R^1{}_n Al_{3-n}$, or $Al_2Y_3R^1{}_3$, wherein $R^1$ represents an alkyl group having from 1 to 20 carbon atoms, Y represents Cl, Br or I, and n is 1 or 2.

20. The method according to claim 1, wherein the additive is selected from the group consisting of polyamines, amines, and amino alcohols.

* * * * *